United States Patent [19]

Bergthaller et al.

[11] 4,055,427

[45] Oct. 25, 1977

[54] PROCESS OF HARDENING A SILVER HALIDE PHOTOGRAPHIC MATERIAL WITH A 1-CARBAMOYLOXYPYRIDINIUM SALT

[75] Inventors: Peter Bergthaller, Cologne; Wolfgang Himmelmann; Wolfgang Sauerteig, both of Leverkusen; Lothar Rosenhahn, Cologne, all of Germany

[73] Assignee: Agfa-Gevaert Aktiengesellschaft, Leverkusen, Germany

[21] Appl. No.: 768,902

[22] Filed: Feb. 15, 1977

Related U.S. Application Data

[63] Continuation of Ser. No. 551,069, Feb. 19, 1975, abandoned.

[30] Foreign Application Priority Data

Feb. 23, 1974  Germany ............................ 2408814

[51] Int. Cl.$^2$ ..................... G03C 1/30; G03C 1/76
[52] U.S. Cl. ................................... 96/67; 96/111; 96/74; 96/77; 260/112 R; 260/117; 106/125; 427/337; 427/338; 427/340; 526/317
[58] Field of Search ............... 96/67, 111, 50 PT, 77, 96/74; 260/295 CA, 247.2 A, 293.59, 287 R, 268 C, 112, 117; 106/125; 427/338, 337, 340; 526/317

[56] References Cited

U.S. PATENT DOCUMENTS 2,950,197  8/1960  Allen et al. .......................... 96/111
3,880,665  4/1975  Himmelmann ....................... 96/111

Primary Examiner—Won H. Louie, Jr.
Attorney, Agent, or Firm—Connolly and Hutz

[57] ABSTRACT

As quick-acting hardeners for layers which contain protein, in particular gelatin layers for photographic purposes carbamoyl oxypyridinium salts are used.

11 Claims, No Drawings

PROCESS OF HARDENING A SILVER HALIDE PHOTOGRAPHIC MATERIAL WITH A 1-CARBAMOYLOXYPYRIDINIUM SALT

CROSS REFERENCE TO RELATED APPLICATION

This application is a continuation of Ser. No. 551,069 filed Feb. 19, 1975, now abandoned.

The invention relates to a process for the hardening of photographic layers which contain protein, preferably gelatine.

Numerous substances have already been described as hardeners for protein and particularly for gelatine; for example metal salts such as chromium, aluminium or zirconium salts, aldehydes and halogen-containing aldehyde compounds, in particular formaldehyde, dialdehydes and mucochloric acid, 1,2- and 1,4-diketones such as cyclohexane-1,2-dione and quinones, chlorides of dibasic organic acids, the anhydrides of tetracarboxylic acid, compounds which contain several reactive vinyl groups, such as vinyl sulphones, acrylamides, compounds containing at least two heterocyclic 3-membered rings which can easily be split, such as ethylene oxide and ethylene imine, polyfunctional methane sulphonic acid esters and bis-α-chloroacyl amido compounds.

High-molecular weight hardeners have recently become known, for example polyacrolein and its derivatives or copolymers as well as alginic acid derivatives. These are used especially as hardeners which are confined to the layer into which they are introduced.

Many of the known compounds, however, are unsuitable for photographic purposes. Some of them are photographically active and therefore unsuitable for hardening photographic materials while others cannot be used because they have a harmful effect on certain of the physical properties of gelatine layers such as their brittleness. Other may cause discoloration or a change in pH during the hardening reaction. Furthermore, it is particularly important for hardening photographic layers that maximum hardening should be reached as soon as possible after drying so that the material which is being hardened does not continuously change its permeability to the developer solution as is the case, for example, with mucochloric acid or formaldehyde.

Some cross-linking agents for gelatine, for example the ethylene imine compounds, also have a deleterious effect on the skin so that for physiological reasons they are unsuitable.

It has long been known to use trichlorotriazine and dichloroaminotriazines as hardeners. Their disadvantages are their relatively high vapour pressure and their physiological action. Water-soluble derivatives which contain carboxyl and sulphonic acid groups and which have been obtained by the reaction of cyanuric chloride with one mol of dimainoalkyl or diaminoacryl sulphonic acid or carboxylic acid do not have these disadvantages and have therefore recently been proposed as hardeners. Their practical utility is, however, limited by the fact that, owing to their high solubility, they decompose when left to stand in aqueous solution and therefore rapidly lose their activity. Hydroxy dichlorotriazine has also been proposed as hardener. Lastly, in a hardener used for photographic layers which contain gelatine it is of the utmost importance both for reasons of preparation of the photographic material and its processing that the onset of the cross-linking reaction should be controllable within certain limits, for example by suitable choice of the drying temperature of the pH.

Compounds which contain two or more acrylic acid amido or vinyl sulphone groups in the molecule are also known as hardeners for photographic gelatine layers, e.g. divinyl sulphone, arylene-bis-vinyl sulphones, N,N',N''-tris-acryloyl-hydrotriazine or methylene-bis-vinyl sulphonamide.

Although hardening of the compounds is quite satisfactory after some time, the compounds are only sparingly soluble in water, with the result that the layer may be unevenly hardened.

The consequences of the undesirable properties of the known hardeners described above are extremely important for photographic purposes because important photographic properties such as the gradation and sensitivity and, in many cases, also the silver covering power depend on the degree of cross-linking of the layer-forming colloid and alter during storage. Although this disadvantage can be attenuated by brief treatment of the solidified layer with ammonia or an amine, it cannot be completely overcome by this method and there is the added disadvantage that aliphatic disulphones have properties which are damaging to the skin.

Carbamoyl pyridinium salts are also known as hardeners with a very good cross-linking action for gelatine and high-molecular weight compounds or mixtures of compounds which contain carboxyl groups and amino groups. The disadvantage of these hardeners is that they are liable to split off pyridine or pyridine derivatives during their reaction with the binder and their commercial applications are therefore limited.

It is an object of this invention to develop quick-acting hardeners for layers which contain protein, in particular gelatine layers for photographic purposes, which hardeners will not have the technical disadvantages of the known compounds.

It is a further object to provide hardening which does not result in increased fog density nor the production of an offensive odor.

A process for hardening photographic layers which contain protein, preferably gelatine, has now been found which is characterised by the use of a carbamoyl oxypyridinium salt as harden.

The hardeners of the present invention correspond to the general formula

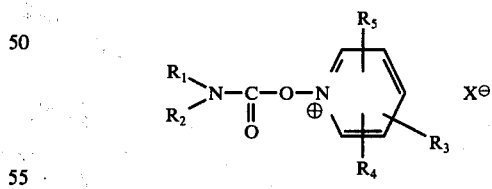

in which $R_1$ represents an alkyl group with preferably 1 to 3 carbon atoms or an aryl group such as a phenyl group, $R_2$ represents an alkyl group with preferably 1 to 3 carbon atoms or the groups

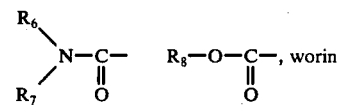

in which $R_6$ represents hydrogen, an alkyl group such as a methyl or ethyl group or an aryl group, $R_7$ represents an alkyl group such as a methyl or ethyl group and $R_8$ represents an alkyl group with preferably 1 to 4 carbon atoms; or $R_1$ and $R_2$ may together represent the atoms required to complete a heterocyclic ring system such as a pyrrolidine-, morpholine-, piperidine-, perhydroazepine-, 1,2,3,4-tetrahydroquinoline- or imidazolidine-2-one- ring or $R_1$ and $R_2$ may together represent the atoms required to complete a piperazine ring in which the second nitrogen atom establishes the connection to a second, similar, molecular residue of the general formula, $R_3$ represents hydrogen, a halogen atom such as chlorine or bromine, an alkyl group such as a methyl or ethyl group, an oxalkyl group with preferably 1 to 3 carbon atoms, a cyano group or a —$CONH_2$ or

alkyl group (such as a methyl or ethyl group)

$R_4$ represents hydrogen or an alkyl group such as a methyl or ethyl group and $R_5$ represents hyrdrogen or a methyl group;

X represents an anion such as a Cl—, $BF_4$— or $ClO_4$— im.

The following compounds have been found to be particularly advantageous. The list is given purely by way of example and is not intended to restrict the scope of the invention.

| Subst. Nr. | $R_1, R_2$ (N-) | Ring structure | $X^\ominus$ | Fp.Zers. | Herstellungs-verfahren | Ausbeute |
|---|---|---|---|---|---|---|
| 1 | CH₃, CH₃ (N—) | —N⁺ (pyridinium) | Cl⁻ | 163–67° | A | 89 % |
| 2 | " | —N⁺—CH₃ | Cl⁻ | 168–70° | A | 85 % |
| 3 | " | —N⁺—CH₃, Cl⁻ | | 86° | A | 89 % |
| 4 | " | —N⁺ with C₂H₅ and CH₃ | Cl⁻ | 90° | A | 80 % |
| 5 | " | —N⁺—Cl | ClO₄⁻ | 100–102° | B | 50 % |
| 6 | " | —N⁺—OC₂H₅ | ClO₄⁻ | 95–100° | B | 60 % |
| 7 | " | —N with OC₂H₅ | ClO₄⁻ | 100–102° | C | 40 % |

-continued

| Subst. Nr. | $\begin{matrix}R_1\\ \phantom{x}\diagdown\\ N-\\ \diagup\\ R_2\end{matrix}$ | $\begin{matrix}R_5\\ \mid\\ -N\diagup\diagdown\\ \phantom{xx}\mid\\ R_4\phantom{x}R_3\end{matrix}$ | $X^\ominus$ | Fp.Zers. | Herstellungs-verfahren | Ausbeute |
|---|---|---|---|---|---|---|
| 8 | $\begin{matrix}CH_3\\ \diagdown N-\\ \diagup\\ CH_3\end{matrix}$ | $-N^+$ pyridinium with $NH-C-OC_2H_5$ substituent | $ClO_4^\ominus$ | 150° | D | 45 % |
| 9 | $\begin{matrix}C_2H_5\\ \diagdown N-\\ \diagup\\ C_2H_5\end{matrix}$ | $-N^+$ pyridinium | $Cl^\ominus$ | 108–110° | A | 70 % |
| 10 | " | $-N^+$ pyridinium, $CH_3$ | $ClO_4^\ominus$ | 64–65° | B | 75 % |
| 11 | " | $-N^+$ pyridinium, $CH_3$ | $ClO_4^\ominus$ | 130–32° | B | 65 % |
| 12 | " | $-N^+$ pyridinium–Cl | $Cl^-$ | 95–100° | A | 72 % |
| 13 | $\begin{matrix}CH_2-CH_2\\ \phantom{xxx}\diagdown N-\\ CH_2-CH_2\diagup\end{matrix}$ | $-N^+$ pyridinium | $Cl^-$ | 114–116° | A | 85 % |
| 14 | $\begin{matrix}CH_2-CH_2\\ \phantom{xxx}\diagdown N-\\ CH_2-CH_2\diagup\end{matrix}$ | $-N^+$ pyridinium, $CH_3$ | $Cl^\ominus$ | 90–92° C | A | 82 % |
| 15 | $\begin{matrix}CH_2-CH_2\\ O\phantom{xx}\diagdown N-\\ \phantom{x}\diagup\\ CH_2-CH_2\end{matrix}$ | $-N^+$ pyridinium | $Cl^\ominus$ | 132° C | A | 92 % |
| 16 | " | " | $BF_4^\ominus$ | 138–40° C | C | 85 % |
| 17 | " | " | $ClO_4^\ominus$ | 150–52° C | C | 88 % |
| 18 | " | $-N^+$ pyridinium, $CH_3$ | $Cl^\ominus$ | 110–13° C | A | 85 % |
| 19 | " | " | $ClO_4^\ominus$ | 140–42° C | C | 85 % |
| 20 | " | $-N$ pyridine, $CH_3$ | $Cl^\ominus$ | 130–32° C | A | 80 % |

-continued

| Subst. Nr. | $\begin{matrix}R_1\\ \phantom{R}N-\\ R_2\end{matrix}$ | pyridinium ring with $R_3, R_4, R_5$ | $X^\ominus$ | Fp.Zers. | Herstellungs-verfahren | Ausbeute |
|---|---|---|---|---|---|---|
| 21 | " | pyridinium, 3-CH₃ | ClO₄⁻ | 144–46° | C | 82 % |
| 22 | " | pyridinium, 4-CH₃ | Cl⁻ | >90° | A | 90 % |
| 23 | " | pyridinium, 4-C₂H₅ | Cl⁻ | 100–102° | A | 81 % |
| 24 | " | pyridinium, 2-CH₃, 4-C₂H₅ | Cl⁻ | 102–104° | A | 87 % |
| 25 | " | pyridinium, 2,4,6-tri-CH₃ | Cl⁻ | 100–102° | A | 90 % |
| 26 | " | pyridinium, 4-OCH₃ | Cl⁻ | 113–115° | A | 80 % |
| 27 | " | pyridinium, 4-OC₂H₅ | Cl⁻ | 115° | A | 60 % |
| 28 | morpholino | " | ClO₄⁻ | 112–14° | C | 57 % |
| 29 | " | pyridinium, 4-OCH(CH₃)₂ | Cl⁻ | 93–95° | A | 72 % |
| 30 | " | pyridinium, 2-OC₂H₅ | Cl⁻ | 65–70° | A | 90 % |
| 31 | " | " | BF₄⁻ | 144–48° | C | 83 % |

-continued

| Subst. Nr. | $R_1$-N-$R_2$ | pyridinium with $R_3$, $R_4$, $R_5$ | $X^\ominus$ | Fp.Zers. | Herstellungs-verfahren | Ausbeute |
|---|---|---|---|---|---|---|
| 32 | " | 2-CN-pyridinium | $Cl^\ominus$ | 80–82° | A | 50 % |
| 33 | " | 3-NHCOCH$_3$-pyridinium | $ClO_4^\ominus$ | 150° | D | 60 % |
| 34 | " | 3-NH–CO–OC$_2$H$_5$-pyridinium | $ClO_4^\ominus$ | 162–63° | D | 60 % |
| 35 | " | 2-CONH$_2$-pyridinium | $ClO_4^\ominus$ | 200° | D | 50 % |
| 36 | (CH$_3$)$_2$CH–N–CH(CH$_3$)$_2$ (with CH$_3$) | pyridinium | $Cl^\ominus$ | 158° | A | 75 % |
| 37 | " | 2-CH$_3$-pyridinium | $Cl^\ominus$ | 138° | A | 80 % |
| 38 | " | 3-CH$_3$-pyridinium | $Cl^\ominus$ | 152–154° | A | 82 % |
| 39 | piperidino (CH$_2$CH$_2$–N–CH$_2$CH$_2$–CH$_2$) | pyridinium | $Cl^\ominus$ | 85–86° | A | 90 % |
| 40 | " | 3-CH$_3$-pyridinium | $ClO_4^\ominus$ | 100° | C | 80 % |
| 41 | " | 4-CH$_3$-pyridinium | $ClO_4^\ominus$ | 80° | C | 75 % |

-continued

| Subst. Nr. | $R_1$\\$R_2$>N— | pyridinium with $R_3, R_4, R_5$ | $X^\ominus$ | Fp.Zers. | Herstellungs-verfahren | Ausbeute |
|---|---|---|---|---|---|---|
| 42 | " | —N⁺—Cl | Cl$^\ominus$ | 104–106° | A | 84 % |
| 43 | (CH₂)₆ ring N— (heptamethyleneimine) | —N⁺— | Cl$^\ominus$ | 76–78° | A | 76 % |
| 44 | indoline-type (N-CH₃, fused benzene with CH₂-CH₂-CH₂) | " | Cl$^\ominus$ | 140–144° | A | 85 % |
| 45 | (C₆H₅)₂N— | " | Cl$^\ominus$ | 160–162° | A | 95 % |
| 46 | " | —N⁺—  CH₃ (2-methyl) | Cl$^\ominus$ | 98–100° | A | 80 % |
| 47 | " | —N⁺— with CH₃ (4-methyl) | Cl$^\ominus$ | 218–220° | A | 90 % |
| 48 | " | —N⁺—CH₃ (2-methyl) | Cl$^\ominus$ | 116° | A | 85 % |
| 49 | " | —N⁺—Cl | Cl$^\ominus$ | 125–128° | A | 80 % |
| 50 | 2,5-dimethylpiperazine (—N— N—) | 2x-N⁺— | 2 Cl$^\ominus$ | 109–112° | A | 75 % |
| 51 | CH₃—NH—C(=O)—N(CH₃)— | —N⁺— | Cl$^\ominus$ | 87–89° | A | 62 % |
| 52 | " | —N⁺— CH₃ (2-methyl) | Cl$^\ominus$ | 105° | A | 80 % |
| 53 | " | —N⁺— CH₃ (3-methyl) | Cl$^\ominus$ | 88–89° | A | 70 % |

-continued

| Subst. Nr. | $R_1, R_2$ N- structure | -N pyridinium $R_3, R_4, R_5$ | $X^\ominus$ | Fp.Zers. | Herstellungsverfahren | Ausbeute |
|---|---|---|---|---|---|---|
| 54 | CH$_3$, CH$_3$ N-C(=O)-N CH$_2$CH$_3$ | -N+ (pyridine) | Cl$^\ominus$ | 168-170° | A | 75 % |
| 55 | CH$_3$, CH$_3$ N-C(=O)-N (CH$_2$)$_2$CH$_3$ | " | Cl$^\ominus$ | 169-173° | A | 65 % |
| 56 | C$_2$H$_5$, C$_2$H$_5$ N-C(=O)-N (CH$_2$)$_2$CH$_3$ | " | Cl$^\ominus$ | 173-180° | A | 80 % |
| 57 | C$_2$H$_5$, C$_2$H$_5$ N-C(=O)-N C$_2$H$_5$ | " | Cl$^\ominus$ | 173-183° | A | 60 % |
| 58 | HN-CH$_2$-CH$_2$-N-C(=O) (ring) | " | Cl$^\ominus$ | 221-223° | A | 70 % |
| 59 | NH-CH$_2$-CH$_2$-N-C(=O) (ring) | -N+ pyridine with CH$_3$ | Cl$^\ominus$ | 180-185° | A | 70 % |
| 60 | phenyl-N(CH$_3$O-C(=O))- | -N⊕ pyridine | Cl$^\ominus$ | 133-134° | A | 90 % |

1-carbamoyloxy- and 1-allophanyloxy pyridinium salts are new compounds, the preparation of which has not previously been described, but they can be obtained by a surprisingly simple method, namely by reacting carbamide chlorides or allophanic acid chlorides with pyridine-N-oxides in aprotic media, sometimes also in alcoholic solution or even in aqueous systems. They are stable for a considerable time at room temperature in the pure state and, even in aqueous solution at pH-values between 5 and 7, they undergo degradation surprisingly slowly. The stability of the new compounds can be even further improved by suitable choice of so-called hard anions, e.g. fluoborate or perchlorate. Whereas the chlorides are in many cases hygroscopic, the fluoborates or perchlorates which are easily obtainable by salt conversion with sodium fluoborate or sodium perchlorate do not show this characteristic.

The N-oxides used as starting materials are known. They are usually prepared from the free bases by oxidation with organic peracids or mixtures of hydrogen peroxides and organic acids. Special representatives of these compounds, e.g. alkoxy pyridine-N-oxides, however, can generally be prepared more satisfactorily by nucleophilic exchange reactions from the corresponding nitropyridine- or halopyridine-N-oxides. Reference may be made in this connection to "Aromatic Amine Oxides" by E. Ochiai, Elsevier 1967 and the references given therein as well as to the publication "Die Einfuhrung von Substituenten in den Pyridin-Ring" by K. Thomas and D. Jerchel in the journal "Angewandte Chemie" vol. 70, pages 719-746 (1958).

N,N-disubstituted carbamide chlorides can be obtained from the corresponding secondary amines by reaction with phosgene. Generally speaking, di- or trisubstituted allophanic acid chlorides are prepared by reacting the corresponding alkyl ureas with phosgene (see H. Ulrich, J. N. Tilley, A. A. R. Sayigh; J. Org. Chem. 29, 2401 (1964) and German Offenlegungsschrift 2 008 116).

Several methods are available for the preparation of the new hardeners according to the invention. These methods will now be illustrated with the aid of six examples.

METHOD OF PREPARATION A

Compound 1

22 g of dimethylcarbamide chloride are added dropwise to 19 g (0.2 mol) of pyridine-N-oxide in 100 ml of anhydrous acetone at 0° to 15° C over a period of 15 minutes. The temperature is kept at 10° to 15° C for a further 45 minutes until the product crystallises. The reaction mixture is then suction-filtered.

The yield was 35g, which was 89% (of the theoretical yield) and the melting point was 163° to 167°° C with decomposition.

Compound 15

30 g of morpholine carbamide chlorine in 50 ml of methylene chloride are added dropwise with stirring to 19 g (0.2 mol) of pyridine-N-oxide in 100 ml of methylene chloride at 0°–15° C. The product is suction-filtered after 60 minutes. The yield was 45 g which was 92% of the theory with a melting point of 132° C (decomposition). According to the analytical results obtained after crystallisation from ethanol/ether, compound 15 corresponds to the monohydrate $C_{10}H_{13}N_2O_3Cl.H_2O$.

Found: C: 45.8 H: 5.7 N: 10.8 Cl: 13.7. Calculated: C: 45.7 H: 5.7 N: 10.7 Cl: 13.5.

METHOD OF PREPARATION B

Compound 11

27g (0.2 mol) of diethylcarbamide chloride in 50 ml of ether are added dropwise with stirring to a solution of 22 g (0.2 mol) of 2-methylpyridine-N-oxide in 100 ml of ether at 0°–10° C. Stirring is continued for a further two hours at 5° C and the reaction mixture is then cooled to 0° C, the supernatant ether is decanted from the oil and 36 g of sodium perchlorate in ethanol are added. After the reaction mixture has been left to stand overnight, it is suction-filtered to remove the precipitated sodium chloride, concentrated by evaporation under vacuum at a temperature below 30° C and left to stand for crystallization.

The yield was 40 g which was 65% of the theory the melting point was 130° to 132° C, with decomposition.

METHOD OF PREPARATION C

Compound 17

20 g of sodium perchlorate is added with as little water as possible to a solution of 24.5 g (0.1 mol) of compound 15 in 60 ml of water. The reaction mixture is left to stand for 30 minutes and then suction-filtered.

The yield was 27 g, and the melting point was 150° to 152° C, with decomposition.

Compound 16

A solution of 24.5 g (0.1 mol) of compound 15 is added to a solution of 14 g of sodium fluoborate in 25 ml of water. The reaction mixture is suction-filtered after 60 minutes. The yield was 25 g, and the melting point was 138° to 140° C with decomposition.

METHOD OF PREPARATION D

Compound 34

30 g (0.2 mol) of morpholine carbamide chloride are added dropwise at room temperature to 36.4 g (0.2 mol) of 3-ethoxycarbonyl aminopyridine-N-oxide in 150 ml of isopropanol. After 10 hours, 30 g of sodium perchlorate in 150 ml of ethanol are added and reaction mixture is left to stand overnight. The precipitated crystals are suction-filtered.

The yield was 50 g, with a melting point of 162° to 163° C with decomposition.

The compounds according to the invention may be added as aqueous or alcoholic solutions to the protein layers before they are cast. Hardening may set in extremely rapidly or moderately soon, depending on the structure of the compound and the concentration employed, but even with the slowest compounds it is completed within one to two days so that no afterhardening effects need be expected. The most rapid hardeners are the allophanyl oxypyridinium salts derived from allophanic acid chlorides, somewhat slower are those carbamyl oxypyridinium salts which are derived from electro-negatively substituted pyridine-N-oxides while the slowest are those representatives of the new class of compounds which are derived from electropostively substituted pyridine-N-oxides. These, and particularly the carbamoyl oxypyridinium salts derived from alkyl pyridine-N-oxides, are so stable that they can be kept in aqueous solution for many days without any loss of their hardening action and they do not increase the viscosity of a gelatine solution at 38° C over several hours.

One particularly advantageous method of applying the hardeners consists of casting the protein solutions before they have been treated with hardener and then coating the resulting layers, optionally when they are already dry, with a solution of the hardening compounds. If desired, however, the compounds may also be added as aqueous solutions while the photographic material is being processed, for example it may be added to a bath of the unhardened or only slightly hardened photographic layers before development.

The compounds described here may be used either singly or as mixtures. They may advantageously be used for hardening photographic layers which, in addition to containing gelatine, also contain other homopolymers and copolymers with carboxyl groups as binders. It is assumed that the compounds according to the invention are capable of effecting cross-linking of gelatine and polymers which contain carboxyl groups.

The term 'photographic layers' is used here in a quite general sense to mean layers which are used in photographic materials, for example light-sensitive silver halide emulsion layers, protective layers, filter layers, antihalation layers, backing layers or photographic auxiliary layers in general.

Light-sensitive emulsion layers for which the hardening process according to the invention is particularly suitable include, for example, those layers which are based on unsensitised emulsions, X-ray emulsions and other spectrally sensitised emulsions. The hardening process according to the invention has also been found satisfactory for hardening the various gelatine layers used for black-and-white and colour photographic processes. The process according to the invention has been found to be particularly suitable for hardening photographic layer combinations which are used for carrying out colour photographic processes, e.g. combinations which contain emulsion layers with colour couplers or emulsion layers which are intended to be treated with solutions which contain colour couplers.

The action of the compounds used according to the invention is not deleteriously affected by the usual photographic additives. The hardeners are also inert towards photographically active substances such as water-soluble and emulsified water insoluble dye components, stabilisers, sensitisers and the like. Moreover, they have no influence on the light-sensitive silver halide emulsions. Furthermore, the compounds can be combined with any compounds from the classes of hardeners previously known, for example formalin, mucochloric acid, triacryloformal, bisvinyl sulphones, bisvinyl sulphonamides, dialdehydes, bischloroacetamides or inorganic salts, e.g. tervalent chromium, tervalent aluminum or zirconium salts.

The layers may contain water-soluble high-polymer compounds in addition to gelatine, in particular polyvinyl alcohol, polyacrylic acid sodium and other copolymers which contain carboxyl groups, polyvinyl pyrrolidone, polyacrylamide or high-molecular weight natural substances such as dextranes, dextrines, starch ether, alginic acid or alginic acid derivatives.

The concentrations at which the hardeners according to the invention are used may vary within wide limits and depend mainly on the particular compound used as hardener.

Satisfactory results are obtained with quantities of 0.5 to 10% by weight and particularly 1 to 5% by weight, based on the dry weight of binder.

The activity of the hardening compounds is assessed by means of the melting point of the layers, which can be determined as follows:

A layer cast on a support is half dipped into water which is continuously heated to a temperature of 100° C. The temperature at which the layer begins to run off the support (formation of streaks) is taken as the melting point or melting-off point. According to this method of measurement, pure protein or gelatine layers which are free from hardener in no case show an increase in melting point. The melting-off point under these conditions is 30° to 35° C.

Swelling of the layer is determined gravimetrically in distilled water at 22° C after 10 minutes' treatment. It is characterised by the swelling factor:

$$\frac{\text{wet weight of layer}}{\text{dry weight of layer}} = \text{swelling factor.}$$

To determine the wet scratch resistance, a metal tip of a specified size is passed over the wet layer and loaded with an increasing weight. The wet scratch resistance is indicated by that weight at which the tip leaves a visible scratching trace on the layer. A high weight corresponds to a high wet scratch resistance.

The compounds according to the invention react surprisingly quickly with proteins after the drying process and thereby enable materials which contain protein to be hardened to an optimum degree within a very short time. This unexpected effect of the compounds is particularly important for hardening photographic materials which contain proteins and polymers with carboxyl groups as binders. The desired degree of hardening can easily be adjusted quite accurately at the stage of preparation of the materials without prolonged storage times and the attendant uncertainties of uncontrollable subsequent hardening.

The hardening compounds used according to the invention are thus distinguished by a hardening reaction which is surprisingly rapid and without after-effects or disadvantages. This property of the compounds makes them eminently suitable for the preparation of very hard photographic layers with a clearly defined and low degree of swelling. This result can be obtained simply by treating the dry or slightly swelled photographic layer with a solution of the hardening compound for a short time and then rapidly drying the layer. Any degree of hardening can easily be achieved in this way. The hardening process does not result in increased fog density in the photographic material, that is the rise of density does not exceed the normal fog density of the unhardened material. At the same time, this processing does not yield an offensive odor. Thus the hardening process of the present inention involving the application of the above-described hardening compounds provides low fogging and an absence of offensive odors.

The following examples serve to explain the invention more fully.

EXAMPLE 1

5% aqueous solutions are prepared from compounds 1, 2, 3, 4, 5, 6, 7, 9, 10, 11, 13, 14, 15, 16, 17, 18, 19, 20, 21, 22, 23, 25, 26, 27, 29, 30, 34, 36, 39, 43, 44, 45, 50, 51, 52, 53, 54, 55, 56, 57, 58. Strips of a gelatine layer 10 μ in thickness which has been cast on a prepared cellulose triacetate substrate and which contains 18% by weight of a cyan coupler of the formula

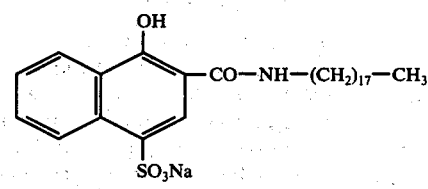

are half dipped into these solutions for 10 seconds and dried in a blast of hot air. The sample strips are then washed with water at 80° C. In all the sample strips, the layer adheres to the half which has been dipped into solution but is washed off the unhardened half.

EXAMPLE 2

Strips of gelatine layers similar to those described in example 1 are treated with aqueous solutions of the compounds according to the invention indicated in the following table and dried as described in example 1. The layer melting points, swelling factor and wet strength are then determined. The results are shown in the table.

For comparison 2 samples in each case of the same unhardened gelatine layer were dipped into a 2.5% solution of tris-acryloyl-hexahydro-s-triazine (A) and mucochloric acid (B) for 1 minute or 3 minutes and the melting point of the layer was determined as already described:

| Comparison sample | Layer-melting point after drying | Swelling factor after 1 day | after 1 day | after 3 days | Wet strength 1 day | 3 days |
|---|---|---|---|---|---|---|
| A | 35° C | | | | | |
| B | 35° C | | | | | |

The results show that the compounds according to the invention will harden unhardened gelatine layers to an extent which is fast to boiling either immediately after drying or, at the latest, after one day's storage and that no subsequent hardening takes place.

| Compound No. | Conc. of aqueous solution | Layer Melting point after drying | Layer Melting point after 1 day | Swelling factor after 1 day A | Swelling factor after 3 days B | Wet strength 1 day A | Wet strength 3 days B |
| --- | --- | --- | --- | --- | --- | --- | --- |
| 1 | 2 % | >100° | >100° | 3.7 | 3.6 | 550 p | 600 p |
| 2 | 2 % | 44° | >100° | 4.2 | 4.2 | 560 p | 560 p |
| 3 | 2 % | 43° | >100° | 4.5 | 4.6 | 450 | 450 |
| 5 | 3 % | 50° | >100° | 4.0 | 3.9 | 400 | 450 |
| 13 | 2 % | 52° | >100° | 4.5 | | 550 | |
| 15 | 2 % | >100° | >100° | 3.7 | 3.8 | 560 | 600 |
| 16 | 3 % | >100° | >100° | 3.6 | 3.8 | 550 | 500 |
| 18 | 2 % | 63° | >100° | 5.6 | 4.5 | 350 | 450 |
| 20 | 2 % | >100° | >100° | 5.4 | 4.8 | 400 | 450 |
| 21 | 3 % | 50° | >100° | 4.0 | 4.0 | 550 | 500 |
| 22 | 2 % | 47° | >100° | 4.8 | 4.7 | 450 | 500 |
| 24 | 3 % | 45° | >100° | | 4.7 | | 450 |
| 25 | 2 % | >100° | >100° | 4.2 | 4.3 | 550 | 600 |
| 26 | 3 % | 47° | >100° | 4.8 | 4.6 | 450 | 650 |
| 27 | 3 % | 53° | >100° | 4.5 | 4.8 | 250 | 350 |
| 39 | 2 % | 59° | >100° | 3.9 | 3.6 | 500 | 650 |
| 44 | 3 % | >100° | >100° | 3.8 | 3.6 | 450 | 450 |
| 47 | 3 % | 74° | >100° | 4.6 | 3.8 | | |
| 48 | 3 % | 45° | >100° | 5.0 | 5.2 | | |
| 51 | 2 % | >100° | >100° | 4.8 | 5.2 | 350 | 300 |
| 52 | 2.6 % | >100° | >100° | 3.0 | 3.2 | 600 | 500 |
| 53 | 2.6 % | >100° | >100° | 3.6 | 4.2 | 450 | 350 |
| 55 | 2.9 % | 59° | >100° | 3.7 | 3.9 | 400 | 400 |
| 58 | 2.5 % | >100° | >100° | 3.3 | 3.8 | 500 | 500 |
| 59 | 2.5 % | >100° | >100° | 3.0 | 3.4 | 750 | 800 |

EXAMPLE 3

Aqueous solutions of the compounds according to the invention are used as described in example 2 in the freshly dissolved state and after 3 hours' storage and 24 hours' storage of the solutions at room temperature for bathing strips of an unhardened gelatine layer similar to that described in example 1. The layers are dried and their properties are determined after 1 day's storage at room temperature. The results are shown in the following table, in which SF = swelling factor and WS = wet strength.

| Compound | Conc. of solution | Properties after storage time of the solution fresh (30 min) | | | 3 hours | | | 24 hours | | |
| --- | --- | --- | --- | --- | --- | --- | --- | --- | --- | --- |
| | | m.pt. | SF | WS | m.pt. | SF | WS | m.pg. | SF | WS |
| 1 | 2 % | >100° | 3.7 | 500 | >100 | 3.7 | 500 | >100 | 3.5 | 600 |
| 2 | 2 % | >100° | 4.2 | 500 | >100 | 4.4 | 500 | >100 | 4.4 | 500 |
| 3 | 2 % | >100° | 4.5 | 450 | >100 | 4.8 | 450 | >100 | 4.7 | 400 |
| 5 | 3 % | >100° | 4.0 | 400 | >100 | 4.4 | 400 | >100 | 4.8 | 400 |
| 13 | 2 % | >100° | 4.4 | 550 | >100 | 4.7 | 550 | >100 | 4.7 | 550 |
| 15 | 2 % | >100° | 3.7 | 500 | >100 | 3.7 | 500 | >100 | 3.8 | 500 |
| 16 | 3 % | >100° | 3.6 | 550 | >100 | 3.5 | 550 | >100 | 3.9 | 450 |
| 18 | 2 % | >100° | 5.6 | 350 | >100 | 5.6 | 350 | >100 | 5.1 | 350 |
| 20 | 2 % | >100° | 5.4 | 400 | >100 | 5.5 | 400 | >100 | 5.3 | 350 |
| 22 | 2 % | >100° | 4.8 | 450 | >100 | 4.8 | 400 | >100 | 4.8 | 400 |
| 25 | 2 % | >100° | 4.2 | 550 | >100 | 4.9 | 500 | >100 | 5.6 | 450 |
| 26 | 3 % | >100° | 4.8 | 450 | >100 | 4.9 | 450 | >100 | 5.7 | 450 |
| 27 | 3 % | >100° | 4.5 | 250 | >100 | 4.8 | 250 | >100 | 4.9 | 200 |
| 39 | 2 % | >100° | 3.9 | 500 | >100 | 4.0 | 500 | >100 | 4.0 | 500 |
| 44 | 3 % | >100° | 3.8 | 450 | >100 | 3.8 | 450 | >100 | 3.9 | 400 |
| 48 | 3 % | >100° | 5.0 | | >100 | 5.0 | | >100 | 5.5 | |
| 55 | 2.9 % | >100° | 3.7 | 400 | >100 | 3.7 | 400 | >100 | 3.8 | 400 |

The results of Example 3 show the excellent stability of the aqueous solutions of the compounds according to the invention even after one day's storage. There is therefore no doubt that the compounds are sufficiently stable for large-scale industrial use.

EXAMPLE 4

Compounds 1, 2, 3, 5, 15, 18, 20, 21, 22, 24, 25, 26, 27, 34, 39, 43, 45, 46, 47, 48, 49, 50 are added to samples of a 10% gelatine solution in quantities of 2%, based on the gelatine. 30 minutes after addition of the compounds, the gelatine is cast on a transparent cellulose triacetate substrate covered with a bonding layer to form gelatine layers 10 $\mu$ in thickness which are then dried. 24 hours after casting, the layer melting point, swelling factors and wet strength values were determined. The results are shown in the following table:

| Compound (2 % based on gelatine) | Layer melting point | Swelling factor | Wet Strength (in pond) |
| --- | --- | --- | --- |
| 1 | 10'100° | 3.4 | 550 p |
| 2 | 10'100° | 3.4 | 450 p |
| 3 | 10'100° | 4.0 | 350 p |
| 5 | 10'100° | 4.4 | 200 p |
| 15 | 10'100° | 3.8 | 550 p |
| 18 | 10'100° | 4.0 | 750 p |
| 20 | 10'100° | 4.8 | 600 p |
| 21 | 10'100° | 4.4 | 500 p |
| 22 | 10'100° | 3.3 | 450 p |
| 24 | 10'100° | 3.8 | 350 p |
| 25 | 10'100° | 5.0 | 250 p |
| 26 | 10'100° | 3.4 | 400 p |
| 27 | 10'100° | 4.2 | 300 p |
| 34 | 10'100° | 4.3 | |
| 39 | 10'100° | 3.5 | 550 p |
| 43 | 10'100° | 4.1 | 450 p |
| 45 | 10'100° | 3.5 | 450 p |
| 46 | 10'100° | 3.1 | 450 p |
| 47 | 10'100° | 4.1 | 450 p |
| 48 | 10'100° | 4.4 | 250 p |
| 49 | 10'100° | 4.2 | 250 p |
| 50 | 10'100° | 3.5 | 450 p |

One part of the casting solution is left to stand at 40° C for 2 hours or 5 hours after their preparation. The viscosities of the solutions are determined in an outflow viscosimeter and the results are compared with those of fresh solutions (outflow time in seconds = ")

| Compound | 10% gelatine (+2% hardener) viscosity fresh | after 2 hours | after 5 hours |
|---|---|---|---|
| 1 | 33" | 33.5" | 34" |
| 2 | 26" | 26" | 26" |
| 3 | 27" | 27" | 28" |
| 5 | 28" | 28" | 28" |
| 15 | 45" | 54" | 75" |
| 18 | 41" | 45" | 45" |
| 20 | 42" | 48" | 59" |
| 21 | 27" | 31" | 36" |
| 24 | 26" | 26" | 27" |
| 25 | 31" | 40" | 41" |
| 26 | 28" | 31" | 35" |
| 27 | 28" | 29" | 29" |
| 34 | 25" | 26" | 27" |
| 39 | 32" | 32" | 34" |
| 43 | 35" | 36" | 41" |
| 46 | 27" | 29" | 29" |
| 47 | 29" | 34" | 37" |
| 48 | 30" | 38" | 46" |
| 49 | 32" | 41" | 41" |

For comparison, the following results are obtained with samples which, instead of containing a compound according to the invention, contain one of the following conventional hardeners:

| Compound | 10% gelatine (+ 2% hardener) viscosity fresh | after 2 hours | after 5 hours |
|---|---|---|---|
| C | 80" | 80" | cross-linked |
| D | 178" | 222" | 268" |
| E | 149" | 156" | 189" |

C: 1-methyl-3(3'-dimethylaminopropyl)-carbodiimide hydrochloride
D: 2,4-dichloro-6-(2'-methoxy)-ethoxy-1,3,5-triazine
E: 2,4-dichloro-6-isopropoxy-1,3,5-triazine.

As the results show, the hardening action of the compounds according to the invention sets in only slowly when they are in a state of solution and it only comes fully into effect after the materials have dried. This means that the hardeners according to the invention can be added to casting solutions even at higher gelatine concentrations without the gelatine being cross-linked within 5 hours or undergoing too much increase in its viscosity. The hardeners according to the invention therefore do not require the use of dosing devices or other technical apparatus designed to add the hardener immediately before casting.

EXAMPLE 5

An unsensitised silver bromide emulsion layer is applied to a paper substrate which has been laminated with polyethylene and covered with a bonding layer, and the emulsion layer is dried. Hardening is carried out by application of a 3% aqueous solution of compounds 1, 2, 13, 15, 16, 18, 20, 22, 25, 44 and 55 according to the invention, followed by drying. For comparison, another emulsion layer is hardened with 0.5% formaldehyde as casting additive and another with 0.5% of 6-methoxyethoxy-2,4-dichlorotriazine.

The samples are stored for 1, 3 and 5 days and then exposed under a step wedge and processed at 25° C as follows:
Developer:
3 g of hydroquinone,
1 g of p-methylaminophenol,
13 g of anhydrous sodium sulphite, 23 g of anhydrous sodium carbonate,
1 g of potassium bromide made up with water to 1000 ml.
Processing:
2 minutes at 25° C.
Short stop bath:
2% acetic acid solution, 1 minute at 25° C.
Fixing bath:
200 g of sodium thiosulphate,
20 g of potassium metabisulphite, water up to 1000 ml
Processing:
5 minutes at 25° C
Washing: 15 minutes at 20° C.
The following results are obtained:

The speed is constant after 1 day when compounds 1, 2, 13, 15, 16, 20, 22, 25 and 44 are used and after 3 days and when compounds 18 and 55 are used. Swelling factor and speed undergo no further changes.

In samples hardened with formaldehyde or alkoxy dichlorotriazine hardeners, some loss in speed could still be observed after 8 days. The final speed was practically the same in all of the samples.

It follows that the compounds according to the invention enable the final hardness to be rapidly obtained and give rise to photographic products with constant speed over a prolonged storage time.

EXAMPLE 6

A colour reversal film is prepared by applying the following layers in succession on a cellulose acetate substrate:

1. A red-sensitive silver iodobromide emulsion (70 g of gelatine, 32 g of silver (96% silver bromide, 4% silver iodide) per kg, 6 g of a cyan coupler of the formula

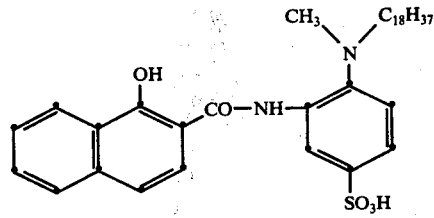

24 g of cyan coupler of the formula

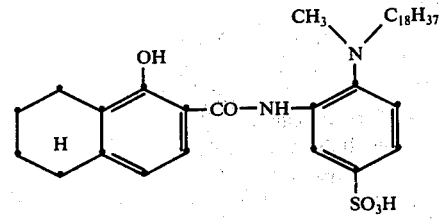

silver application 0.9 g/m²;

2. An interlayer containing 3 g of polymeric white coupler of the formula

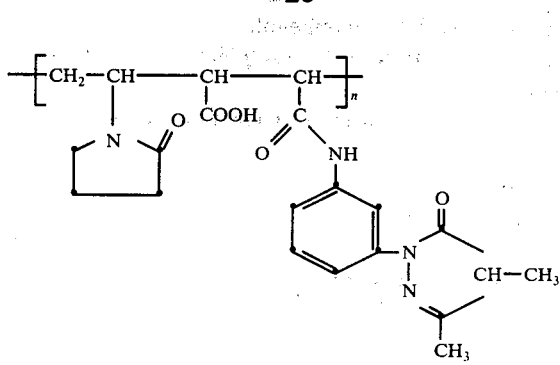

per kg of casting solution;

3. A green-sensitised silver iodobromide emulsion (96% AgBr, 4% AgI) containing, per kg of emulsion, 70 g of gelatine, 32 g of silver, 25 g of a magenta coupler of the formula

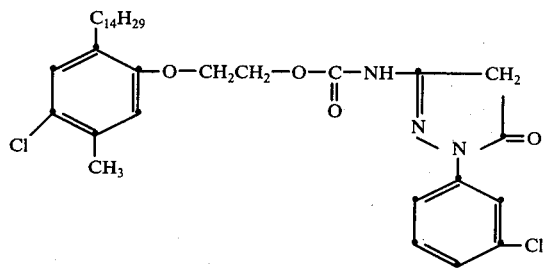

silver application 0.9 g/m²;

4. A silver filter layer containing colloidal silver obtained from 1.8 g of silver nitrate in 12 g of gelatine per 1000 ml. Colour density 0.6 (measured behind blue filter);

5. A non-sensitised silver iodobromide emulsion with an iodide content of 2%, containing, per kg, 110 g of gelatine, 70 g of silver and 45 g of a yellow coupler of the formula

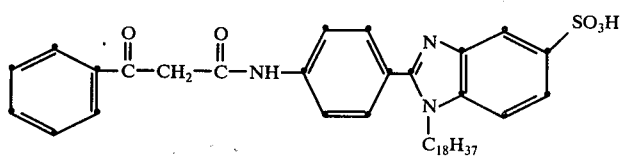

silver application 1.3 g/m².

The material is hardened by bathing it in a 2%-solution of compound 15.

A second reversal material is built up in a similar manner, with the difference that the red-sensitised and the green-sensitised emulsion layer and the interlayers contain 0.4% of 1,3,5-tris-acryloyl-hexahydro-5-triazine, based on gelatine, and the non-sensitised layer contains 0.6% of tris-acryloylhexahydro-5-triazine as hardener.

Two lengths of film are obtained, from each of which a sample is exposed behind a graduated wedge after 1 day, 8 days and 28 days' storage at room temperature and then subjected to reversal processing as described below.

One further sample from each film length is stored moist at 35° C and 80% relative humidity for 3 days. Processing: 20° C.

Black-and-white developer: (7 minutes)

300 ml of distilled water,
2g of sodium hexametaphosphate,
2.3 g of p-methylaminophenol,
50 g of sodium sulphite anhydrous,
6.6 g of hydroquinone,
50 g of sodium carbonate anhydrous,
3.5 g of potassium thiocyanate,
1.8 g of potassium bromide,
0.008 g of potassium iodide, made up with water to 1000 ml: pH 10.

Short stop bath: (5minutes)
300 ml of distilled water,
30 g of sodium acetate crysrallised,
5 ml of acetic acid made up to 100 ml with water: pH 5.

Washing: 10 minutes
Reversal exposure: 2 minutes
Colour development: 18 minutes
300 ml of distilled water,
2 g of nitrilotriacetic acid,
3.5 g of N,N-diethyl-p-phenylenediamine,
20 g of trisodium phosphate,
0.7 g of potassium bromide,
0.8 g of hydroxylamine hydrochloride, made up to 1000 ml with water: pH 11.7.

Washing: 5 minutes,
Bleaching bath: 5 minutes
8 g of potassium ferricyanide, 20 g of potassium bromide, 12 g of disodium phosphate made up to 1000 ml with water, adjusted to pH 5.2 with acetic acid.

Washing: 5 minutes
Fixing bath: 5 minutes 150 g of ammonium thiosulphate,
10 g of sodium sulphite anhydrous,
2 g of sodium hexametaphosphate made up to 1000 ml with water: pH 7.

Final washing: 5 minutes.

The photographic assessment shows that the sample which has been hardened with compound 15 according to the invention reaches it final speed after only 1 day and has been hardened fast to boiling. No loss of speed by subsequent further hardening is observed.

The sample which has been hardened with conventional hardener has a layer melting point of 40° C after 1 day and 8 days, and the sample which has been hardened for 28 days shows a distinct loss in speed compared with that of the fresh sample. The general speed of the sample when fresh is higher than that of the material which has been hardened with the compound according to the invention.

Both film samples have the same final speed after 3 days' storage in a moist atmosphere. Reversal fog, maximum density loss and gradation changes do not occur.

What is claimed is:

1. A process for providing a hardened layer in a photographic material containing a light sensitive silver halide emulsion layer and at least one layer containing a binder selected from the group consisting of gelatin and homopolymers and copolymers which contain carboxyl groups coated on a support wherein the improvement comprises applying to the binder-containing layer a hardening amount of a 1-carbamoyloxypyridinium salt of the formula

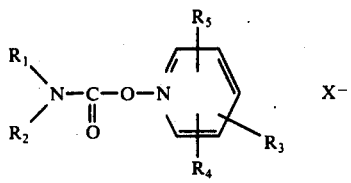

in which
R₁ represents a lower alkyl or aryl group,
R₂ represents a lower alkyl group or a group

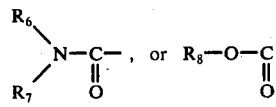

in which
R₆ represents hydrogen, or a lower alkyl or aryl group,
R₇ represents a lower alkyl group and
R₈ represents a lower alkyl group; or
R₁ and R₂ together represent the atoms required to complete a heterocyclic ring selected from the group consisting of pyrrolidine, morpholine-, piperidine-, perhydroazepine-, 1,2,3,4-tetrahydroquinoline- or imidazolidine-2-one ring, or
R₁ and R₂ together represent the atoms required to complete a piperazine ring in which the nitrogen that completes said piperazine ring is a member of the carbamoyl group of a second carbamoyloxypyridinium group,
R₃ represents hydrogen or halogen, or a lower alkyl, lower oxyalkyl, cyano, CONH₂ or

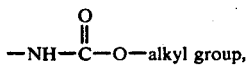

R₄ represents hydrogen or a lower alkyl group,
R₅ represents hydrogen or a lower alkyl group and represents an anion.

2. A process according to claim 1 wherein the photographic material is a multi-layered color photographic material.

3. A process according to claim 1 characterised in that the hardener is applied as a coating from aqueous solution.

4. A process according to claim 1 characterised in that the hardener is applied as a coating from alcoholic solution.

5. A process according to claim 1 characterized in that the hardener is applied as a coating from aqueous alcoholic solution.

6. A process according to claim 1 characterised in that the hardener is used in quantities of 0.5 to 10% by weight, based on the weight of the binder in the casting solution of the layer which is to be hardened.

7. A process according to claim 1 characterised in that the 1-carbamoyloxypyridinium salt is applied as a 0.2 to 10% solution before the material is processed.

8. A process according to claim 1 characterised in that the layer which is to be hardened is coated with a 0.2 to 5% solution of the 1-carbamoyloxypyridinium salt and is then dried.

9. A process according to claim 1 wherein the 1-carbamoyloxypyridinium salt is a compound of the general formula of claim 1 in which R₁ and R₂ together represent the atoms required to complete a morpholine ring, R₃ and R₅ are hydrogen atoms and R₄ stands for methyl.

10. A process according to claim 1 wherein the 1-carbamoyloxypyridinium salt is a compound of the general formula of claim 1 in which R₁ and R₂ together represent the atoms required to complete a morpholine ring, R₃ is ethyl, R₄ is hydrogen and R₅ stands for methyl.

11. A process according to claim 1 wherein the 1-carbamoyloxypyridinium salt is a compound of the general formula of claim 1 in which R₁ and R₂ together represent the atoms required to complete a morpholine ring, and R₃, R₄ and R₅ is methyl.

* * * * *

UNITED STATES PATENT AND TRADEMARK OFFICE
CERTIFICATE OF CORRECTION

PATENT NO. : 4,055,427
DATED : October 25, 1977
INVENTOR(S) : Bergthaller et al

It is certified that error appears in the above-identified patent and that said Letters Patent are hereby corrected as shown below:

Column 1, line 57, "dimainoalkyl" should read
    -- diaminoalkyl -- .
Column 1, line 57, "diaminoacryl" should read
    -- diaminoaryl -- .
Column 5, compound 13 should read as follows:

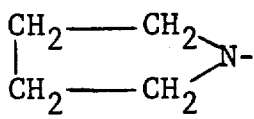

Column 26, line 3 should read --

X represents an anion. --

*Signed and Sealed this*

Eighteenth Day of April 1978

[SEAL]

*Attest:*

RUTH C. MASON
*Attesting Officer*

LUTRELLE F. PARKER
*Acting Commissioner of Patents and Trademarks*